United States Patent
De Simone

(10) Patent No.: US 9,439,953 B2
(45) Date of Patent: *Sep. 13, 2016

(54) COMPOSITIONS COMPRISING ALKALINE SPHINGOMYELINASES FOR USE AS A DIETETIC PREPARATION, FOOD SUPPLEMENT OR PHARMACEUTICAL PRODUCT AND METHODS FOR USING THEM

(71) Applicant: VSL PHARMACEUTICALS INC., Rome (IT)

(72) Inventor: Claudio De Simone, Rome (IT)

(73) Assignee: VSL PHARMACUETICALS, INC., Rome (IT)

( * ) Notice: Subject to any disclaimer, the term of this patent is extended or adjusted under 35 U.S.C. 154(b) by 87 days.

This patent is subject to a terminal disclaimer.

(21) Appl. No.: 14/164,861

(22) Filed: Jan. 27, 2014

(65) Prior Publication Data

US 2014/0140971 A1 May 22, 2014

Related U.S. Application Data

(60) Division of application No. 11/105,592, filed on Apr. 14, 2005, now Pat. No. 8,697,051, which is a continuation-in-part of application No. 10/964,770, filed on Oct. 15, 2004, now abandoned, which is a continuation of application No. 09/960,652, filed as application No. PCT/IT00/00230 on Jun. 19, 1999, now abandoned.

(30) Foreign Application Priority Data

Jun. 19, 1999 (IT) .................. RM99A0376

(51) Int. Cl.
| | | |
|---|---|---|
| C12N 1/20 | (2006.01) |
| A61K 38/46 | (2006.01) |
| A23L 1/03 | (2006.01) |
| A23L 1/30 | (2006.01) |
| A23L 1/305 | (2006.01) |
| A61K 35/744 | (2015.01) |
| A61K 35/745 | (2015.01) |
| A61K 35/747 | (2015.01) |
| C12N 9/16 | (2006.01) |
| A61K 35/74 | (2015.01) |
| A61K 45/06 | (2006.01) |
| A61K 38/00 | (2006.01) |

(52) U.S. Cl.
CPC ............ *A61K 38/465* (2013.01); *A23L 1/034* (2013.01); *A23L 1/0345* (2013.01); *A23L 1/30* (2013.01); *A23L 1/3014* (2013.01); *A23L 1/3058* (2013.01); *A61K 35/74* (2013.01); *A61K 35/744* (2013.01); *A61K 35/745* (2013.01); *A61K 35/747* (2013.01); *A61K 45/06* (2013.01); *C12N 9/16* (2013.01); *C12Y 301/04012* (2013.01); *A23V 2002/00* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,071,037 A | 1/1978 | Scheinberg | |
| 4,085,228 A | 4/1978 | Reinbold | |
| 4,158,607 A | 6/1979 | Kalinowski et al. | |
| 4,524,136 A | 6/1985 | Lee et al. | |
| 5,716,615 A | 2/1998 | Cavaliere Vesely et al. | |
| 5,851,782 A | 12/1998 | Hannun et al. | |
| 5,912,152 A | 6/1999 | Hara et al. | |
| 6,572,854 B1 * | 6/2003 | De Simone | C12R 1/24 424/780 |
| 7,052,688 B2 * | 5/2006 | De Simone | A61K 8/99 424/93.45 |
| 7,147,847 B2 * | 12/2006 | De Simone | C12R 1/24 424/780 |
| RE39,585 E * | 4/2007 | DeSimone | A23L 1/0345 424/93.3 |
| 7,628,981 B2 * | 12/2009 | De Simone | A23L 1/3014 424/93.3 |

FOREIGN PATENT DOCUMENTS

| | | |
|---|---|---|
| FR | 2729079 | 7/1996 |
| GB | 2037160 A | 7/1980 |
| JP | 63-216813 | 9/1988 |

OTHER PUBLICATIONS

Gionchetti et al. Gastroenterology, Aug. 2000, 119(2):305-309.*
Hetland et al.(Scand J Clin Lab Invest, 1982, 42, pp. 57-61.*
Sugimoto et al. Agric Biol Chem, 1983, 47(6), pp. 1201-1206.*
Sjoqvist et al. Gastroenterology, 1999, 116(4) (Part 2), p. A505.*
De Angelis et al., "VSL#3 probiotic preparation has the capacity to hydrolyze gliadin polypeptides responsible for celiac sprue", Biochim. Biophys. Acta 1762:80-93 (2005).
Di Marzio et al., "Detection of alkaline sphingomyelinase activity in human stool: Proposed role as a new diagnostic and prognostic marker of colorectal cancer", Cancer Epidemiol Biomarkers Prev. 14:856-862 (2005).
Duan et al., "Alkaline sphingomyelinase activity in rat gastrointestinal tract: Distribution and characteristic", Biochim. Biophys. Acta 1259:49-55 (1995).

(Continued)

Primary Examiner — Vera Afremova
(74) Attorney, Agent, or Firm — Greer, Burns & Crain, Ltd.; Gregory P. Einhorn

(57) ABSTRACT

The invention relates to a composition which, depending on the user, may be taken as a nutritional, dietetic or strictly therapeutic preparation, comprising as its active substance alkaline sphingomyelinase which is capable of preventing or treating various pathological conditions including cancerous processes, inflammatory processes of the intestine, hypercholesterolaemia and infections with *Helicobacter pylori*.

20 Claims, 3 Drawing Sheets

(56) References Cited

OTHER PUBLICATIONS

Duan el al., "Distribution of alkaline sphingomyelinase activity in human beings and animals", Digestive Dis. Sci., 41:1801-1806 (1996).
Duan et al., "Alkaline sphingomyelinase: An old enzyme with novel implications", Biochim. Biophys. Acta 1761:281-291 (2006).
Hetland et al., "Phospholipase C from bacillus cereus has sphingomyelinse activity", Scand. J. Clin. Invest., 1982, 42:57-61.
Lin et al., "Identification of neutral and acidic sphingomyelinase in Helicobacter pylori", FEBS Letters, 1998, 423:249-253.
Pomerantsev et al., "Phosphatidylcholine-specific phospholipase C and sphingomyelinase activities in bacteria of the Bacillus cereus group", Infect. Immun., 71:6591-6606 (2003).
Sugimoto et al., "Hydrolysis of Phosphatidyl Ethanolamine by Cell Fractions of *Streptococcus lactis*", Agric. Biol. Chem., 47(60), 1201-1206, 1983.
Titball et al., "Hemolytic and sphingomyelinase activities of Clostridium perfringens alpha-toxin are dependent on a domain homologous to that of an enzyme from the human arachidonic acid pathway", Infect. Immun., 59:1872-1874 (1991).
Wu et al.. "Intestinal alkaline sphingomyelinase hydrolyses and inactivates platelet-activating factor by a phospholipase C activity", Biochem. J. 394:299-308 (2006).

* cited by examiner

COMPOSITIONS COMPRISING ALKALINE SPHINGOMYELINASES FOR USE AS A DIETETIC PREPARATION, FOOD SUPPLEMENT OR PHARMACEUTICAL PRODUCT AND METHODS FOR USING THEM

RELATED APPLICATIONS

This application is a divisional of U.S. patent application Ser. No. 11/105,592, filed Apr. 14, 2005; which is a continuation-in-part of application U.S. Ser. No. 10/964,770, filed Oct. 15, 2004 (abandoned); which is a continuation of application U.S. Ser. No. 09/960,652, filed Sep. 24, 2001 (abandoned) which is a continuation of Patent Convention Treaty (PCT) International Application Serial No. PCT/IT00/00230, filed Jun. 7, 2000; which claims benefit of priority to ITALY Patent Application Serial No. RM99A000376, filed Jun. 19, 1999. The aforementioned applications are expressly incorporated herein by reference in their entirety and for all purposes.

The present invention relates to the use of alkaline sphingomyelinase, preferably of bacterial origin, for the preparation of compositions intended for nutritional, dietetic or strictly therapeutic use, together with the compositions made in this way.

BACKGROUND OF THE INVENTION

Consequently, these compositions may be in the form of and may act as food supplements, dietetic bases or medicinal preparations proper, according to whether they are intended to act as bases or prophylactic treatments or as therapeutic preparations proper, depending on the particular individuals for whom the composition is intended.

Three different types of sphingomyelinase (SMase) have so far been identified.

There is an acidic sphingomyelinase, which is a lysosomal enzyme (with an optimum pH of 4.5-5), deficiency of which causes Niemann-Pick disease, and there is a neutral sphingomyelinase, with an optimum pH of 7.5, for which two iso-forms have been described. One of these iso-forms is located in the cytoplasmic membrane and depends on magnesium, while the other is contained in the cytosol and is independent of cations. Both the acidic and the neutral sphingomyelinase are found in many tissues and cells and are ubiquitous enzymes, regulating numerous cell functions.

The third type is called alkaline sphingomyelinase, because it is mainly active at pH 9. It is independent of magnesium and has been found both in intestinal brush borders and in the bile. Alkaline sphingomyelinase does not occur in the stomach, duodenum or pancreas but it is found in the intestine, especially in the distal part of the jejunum. A marked alkaline sphingomyelinase activity has also been observed in the colon and the rectum. High levels of alkaline sphingomyelinase are also found in the bile, but this seems to be peculiar to human beings. This twofold source of sphingomyelinase makes human beings very efficient in comparison with other creatures as regards the hydrolysis of sphingomyelin (SM) introduced via the diet. It has hitherto been thought that alkaline sphingomyelinase cannot be produced by intestinal bacteria, because no differences have been found between conventional and germ-free animals (see R. D. Duan, Scand. J. Gastroenterology, 33 (1998) pp. 673-683).

Apart from the alkaline sphingomyelinase that is present in the intestine and that present in the bile, no other alkaline sphingomyelinases are known that could be used to produce compositions intended for nutritional, dietetic or strictly therapeutic use. Moreover, acidic and neutral sphingomyelinase cannot be employed owing to their differing characteristics (see the following table).

TABLE

| Location | Acidic SMase lysosomes | Neutral SMase cytoplasmic membrane | Alkaline SMase human intestine and bile |
|---|---|---|---|
| Optimum pH | 5.5 | 7.4 | 9 |
| $Mg^{++}$-dependence | No | Yes | No |
| Trypsin resistance | No | No | Yes |
| Thermal stability | <40° C. | — | <50-60° C. |
| Substrate | endocytic SM | membrane SM | SM in food |

The use of sphingomyelinase for cosmetic and dermatological purposes is already known.

Japanese Patent No. 63 216,813 describes cosmetic compositions that contain sphingomyelinase and are intended for counteracting the physiological decrease of this enzyme that occurs in the skin on ageing, and for promoting its transformation into ceramide which, in turn, has a beneficial moisturizing effect on the epidermis.

International Patent Application PCT WO 98/22,082 describes the use of sphingomyelinase for the preparation of dermatological compositions suitable for treating skin disorders such as dermatitis, psoriasis, ichthyosis and similar conditions. Furthermore, this PCT application describes the preparation of sphingomyelinase from strains of Gram-negative bacteria, Gram-positive bacteria and lactic acid bacteria, with clear advantages over the previously known processes, which use the organs of higher animals, such as the brain and liver, as starting materials.

DESCRIPTION OF THE INVENTION

Figure 1:
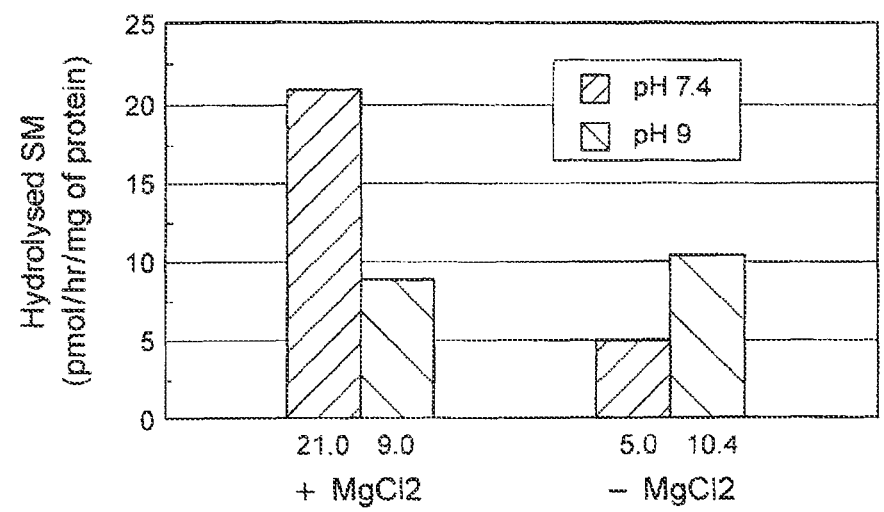
FIG. 1 is a graph showing SMase activity found in *Streptococcus thermophilus;*

It has now been found, surprisingly, that some bacteria possess high levels of alkaline sphingomyelinase, and that their ingestion can be beneficial for the host. These bacteria can be ingested live or in the form of extracts, provided that these are enzymatically active, possibly in combination with other bacteria such as lactic acid bacteria, with SM and/or with foods containing SM.

One of the objects of the present invention is therefore to provide a dietetic, nutrient or pharmaceutical composition that comprises alkaline sphingomyelinase in an amount that is sufficient to exert a dietetic, nutritional or therapeutic effect in an individual who needs it thereby increasing the levels of SMase in the host, particularly humans.

In particular, this composition is suitable for the prevention and/or treatment of disorders connected with intestinal development, cancerous processes, disorders of the immune response, inflammatory and apoptosic processes of the intestine and its associated structures, disorders connected with cholesterol synthesis, disorders due to the hydrophobic nature of the surfaces of the gastrointestinal tract, allergic disorders of the gastro-intestinal tract, disorders relating to digestive processes, inflammatory intestinal diseases, polyposis, in particular familial polyposis, hypercholesterolaemia, infections with *Helicobacter pylori*, disorders of neonatal growth, disorders connected with intestinal homeostasis and diseases of the central and peripheral nervous systems.

The composition is also useful for use in pediatric diets and/or in enteral alimentation. In pediatric diets the composition may be administered, for example, in combination with artificial milk, condensed milk, soybean milk, powdered milk, partially humanized milk and baby foods in general.

There is no need to isolate, purify and characterize alkaline sphingomyelinase from bacteria in order to obtain a therapeutic or beneficial result. The bacteria may be administered per se, either live or lyophilized or sonicated.

The composition preferably contains alkaline sphingomyelinase of bacterial origin, and the bacteria containing the alkaline sphingomyelinase are chosen from amongst Gram-positive bacteria, Gram-negative bacteria and lactic acid bacteria, or from mixtures thereof.

More especially, the alkaline sphingomyelinase of the composition is obtained from lactic acid bacteria, and these are chosen from the group comprising *Lactobacillus acidophilus, Lactobacillus brevis, Lactobacillus buchneri, Lactobacillus casei, Lactobacillus catenaforme, Lactobacillus cellobiosus, Lactobacillus crispatus, Lactobacillus curvatus, Lactobacillus delbrueckii, Lactobacillus fermentum, Lactobacillus jensenii, Lactobacillus leichmannii, Lactobacillus minutus, Lactobacillus plantarum, Lactobacillus rogosae, Lactobacillus salivarius, Bifidobacterium adolescentis, Bifidobacterium angulatum, Bifidobacterium bifidum, Bifidobacterium breve, Bifidobacterium catenulatum, Bifidobacterium dentium, Bifidobacterium eriksonii, Bifidobacterium infantis, Bifidobacterium longum, Bifidobacterium plantarum, Bifidobacterium pseudocatenulatum, Bifidobacterium pseudolongum, Streptococcus lactis, Streptococcus raffinolactis* and *Streptococcus thermophilus*.

The particularly preferred strain amongst these lactic acid bacteria providing alkaline sphingomyelinase is *Lactobacillus brevis* CD2, filed on Feb. 6, 1998 under access No. DSM 11,988 in the German Collection of Micro-organisms and Cell Cultures (DSM) in Braunschweig, Germany ("Deutsche Sammlung von Mikroorganismen and Zellkulturen GmbH") under the Budapest Treaty, or mutants or derivatives thereof.

According to a preferred embodiment of the invention, the lactic acid bacteria providing alkaline sphingomyelinase are used in the composition as live, lyophilized or sonicated bacteria.

The composition preferably contains from $1 \times 10^2$ to $1 \times 10^{13}$ CFUs of lactic acid bacteria per gram of composition.

A particularly preferred composition contains $200 \times 10^9$ *Streptococcus thermophilus*, $150 \times 10^9$ *Bifidobacteria* and $4 \times 10^9$ *Lactobacillus acidophilus* per gram of composition.

The composition according to the invention can also contain bile acids, in particular ursodeoxycholic acid, pectin, sphingomyelin or its compounds, drugs or foods containing sphingomyelin, arginine deiminase, fatty acids, polyunsaturated fatty acids, non fermented sugars, in particular lactulose, cholesterol inhibitors, ceramidase inhibitors, protease inhibitors, immunomodulators, anti-carcinogenic agents, vitamins, growth factors, surfactants, cereals, fibre, emulsifiers, stabilizers, lipids, antioxidants, preservatives, free-radical neutralizers and/or vaso-protectors.

The composition of the invention can be administered orally as a food supplement or orally or parenterally as a drug.

The invention also relates to the use of alkaline sphingomyelinase preferably of bacterial origin for the preparation of a dietetic, nutrient or pharmaceutical composition suitable for the prevention and/or treatment of disorders connected with intestinal development, cancerous processes, disorders of the immune response, inflammatory and apoptosic processes of the intestine and its associated structures, disorders connected with cholesterol synthesis, disorders due to the hydrophobic nature of the surfaces of the gastrointestinal tract, allergic disorders of the gastro-intestinal tract, disorders relating to digestive processes, inflammatory intestinal diseases, polyposis, in particular familial polyposis, hypercholesterolaemia, infections with *Helicobacter pylori*, disorders of neonatal growth, disorders connected with intestinal homeostasis and diseases of the central and peripheral nervous systems.

This composition is also useful for use in pediatric diets and/or in enteral alimentation. In pediatric diets the composition may be administered, for example, in combination with artificial milk, condensed milk, soybean milk, powdered milk, partially humanized milk and baby foods in general.

The alkaline sphingomyelinase used is preferably of bacterial origin, and the bacteria containing it are chosen from amongst Gram-positive bacteria, Gram-negative bacteria and lactic acid bacteria, or from mixtures thereof.

More especially, the lactic acid bacteria providing alkaline sphingomyelinase used are chosen from the group comprising *Lactobacillus acidophilus, Lactobacillus brevis, Lactobacillus buchneri, Lactobacillus casei, Lactobacillus catenaforme, Lactobacillus cellobiosus, Lactobacillus crispatus, Lactobacillus curvatus, Lactobacillus delbrueckii, Lactobacillus fermentum, Lactobacillus jensenii, Lactobacillus leichmannii, Lactobacillus minutus, Lactobacillus plantarum, Lactobacillus rogosae, Lactobacillus salivarius, Bifidobacterium adolescentis, Bifidobacterium angulatum, Bifidobacterium bifidum, Bifidobacterium breve, Bifidobacterium catenulatum, Bifidobacterium dentium, Bifidobacterium eriksonii, Bifidobacterium infantis, Bifidobacterium longum, Bifidobacterium plantarum, Bifidobacterium pseudocatenulatum, Bifidobacterium pseudolongum, Streptococcus lactis, Streptococcus raffinolactis* and *Streptococcus thermophilus*.

The particularly preferred strain providing alkaline sphingomyelinase amongst these lactic acid bacteria is *Lactobacillus brevis* CD2, filed on Feb. 6, 1998 under access No. DSM 11,988 in the German Collection of Micro-organisms and Cell Cultures (DSM) in Braunschweig, Germany ("Deutsche Sammlung von Mikroorganismen and Zellkulturen GmbH") under the Budapest Treaty, or mutants or derivatives thereof.

According to a preferred embodiment of the invention, the lactic acid bacteria providing alkaline sphingomyelinase are used in the composition as live, lyophilized or sonicated bacteria.

The composition used preferably contains from $1\times10^2$ to $1\times10^{13}$ CFUs of lactic acid bacteria per gram of composition.

A particularly preferred composition contains $200\times10^9$ Streptococcus thermophilus, $150\times10^9$ Bifidobacteria and $4\times10^9$ Lactobacillus acidophilus per gram of composition.

The following experiments were carried out to confirm the presence and efficacy of alkaline sphingomyelinase in the bacteria according to the present invention. These experiments involved the detection of alkaline sphingomyelinase, the enzyme responsible for the formation of ceramide in human skin.

Methods

Assay of Acidic, Neutral and Alkaline Sphingomyelinase in Lactic Acid Bacteria and in Intestinal Biopsy Material 10 mg of lyophilized Streptococcus thermophilus bacteria were suspended in 500 µl of a buffer containing 50 mM Tris-HCl, pH 7.4, 10 mM $MgCl_2$, 2 mM EDTA, 5 mM DTT, 0.1 mM $Na_3VO_4$, 0.1 mM $Na_2MoO_4$, 30 mM p-nitrophenyl phosphate, 10 mM β-glycerophosphate, 750 mM ATP, 1 µM PMSF, 10 µM leupeptin, 10 µM pepstatin (from Sigma Chemical Co.) and 0.2% Triton X-100 (to assay the activity of neutral SMase) or 500 µl of 0.2% Triton X-100 (to assay the activity of acidic SMase). To assay the alkaline SMase, the bacteria and the (homogenized) intestinal biopsy material were suspended in a 0.25 M sucrose buffer containing 5 mM $MgCl_2$, 0.15 M KCl, 50 mM $KH_2PO_4$, 1 mM PMSF and 1 mM benzamidine (pH 7.4). The samples prepared in this way were then subjected to lysis by sonication (for 30 min during which, 10-sec "on" periods alternated with 10-sec "off" periods), using a Vibracell sonicator (Sonic and Materials Inc., Danbury, Conn.). The sonicated samples were then centrifuged for 30 min at 14,000 rpm at 4° C., the supernatant was removed, and the protein concentration was determined with a kit made by Bio-Rad Laboratories, (Richmond, Calif.).

To determine the neutral SMase, 100 µg of the sample were incubated for 2 hours at 37° C. in a buffer (final volume: 50 µl) containing 50 mM Tris-HCl, 1 mM $MgCl_2$, pH 7.4, and 2.25 µl of [N-methyl-$^{14}$C]-sphingomyelin (SM) (0.2 µCi/ml, specific activity: 56.6 mCi/mmol, Amersham).

To determine the activity of the acidic sphingomyelinase, 100 µg of the bacterial lysate were incubated for 2 hours at 37.degree. C. in a buffer (final volume: 50 µl) containing 250 mM sodium acetate, 1 mM EDTA, pH 5.0, and 2.25 µl of [N-methyl-$^{14}$C]-SM.

To assay the alkaline SMase, the samples were added to 375 µl of Tris-EDTA buffer (pH 9) to a final volume of 0.4 ml, containing 50 mM Tris, 0.15 M NaCl, 2 mM EDTA and a mixture of 3 mM bile salts with a TC:TDC:GC:GCDC molar ratio of 3:2:1.8:1. This mixture of bile salts had been found to possess the highest stimulatory effect on alkaline SMase. The addition of EDTA to the buffer served to inhibit the activity of neutral SMase, which is $Mg^{++}$-dependent with an optimum pH of 7.5. The $^{14}$C-SM was dissolved in ethanol, dried under nitrogen and suspended in the assay buffer, containing a mixture of 3% Triton X-100 and 3 mM bile salts.

The reaction was terminated by the addition of 2 ml of a 2:1 mixture of chloroform and methanol. The phospholipids were extracted and analysed on TLC plates, while the hydrolysis of the SM was quantified by autoradiography and liquid scintillation counting. The SMase present in the sonicated bacteria and in the intestinal biopsy material was expressed as pmol of SM hydrolysed per hour per milligram of protein.

Activity of SMase from Streptococcus thermophilus

FIG. 1 shows the activity levels of sphingomyelinase in sonicated lactic acid bacteria. No activity due to acidic SMase was found, but appreciable levels of both neutral and alkaline SMase were observed in the bacterial samples tested under the experimental conditions used (various pH values and with and without $MgCl_2$).

Alkaline SMase Found in Intestinal Biopsy Material

Figure 2:
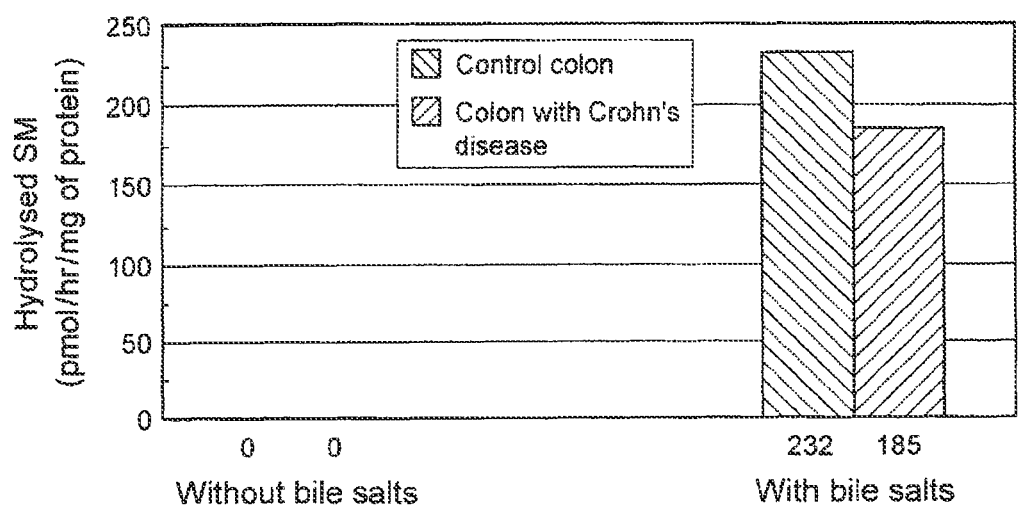
FIG. 2 is a graph showing alkaline SMase found in intestinal biopsy material.

FIG. 2 shows that the analysis of SMase activity in the intestinal biopsy samples showed a high activity of alkaline SMase of the kind dependent on bile salts, which could not be detected in the absence of bile salts. The levels of enzymatic activity in the tissues of a patient suffering from Crohn's disease showed a lower level of alkaline SMase than the control sample.

Effect of Streptococcus thermophilus on Intestinal Alkaline SMase

Figure 3:
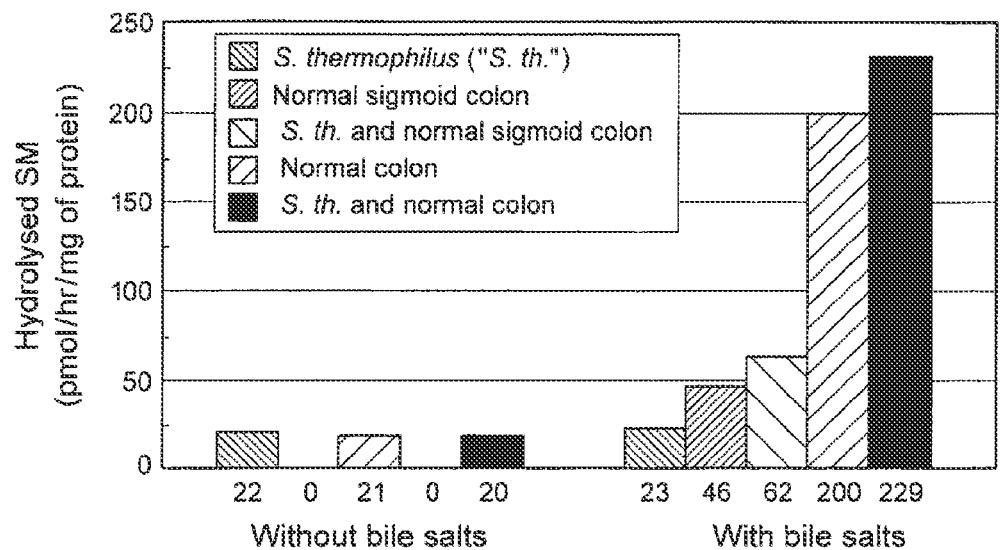
FIG. 3 is a graph showing an effect of *Streptococcus thermophilus* on intestinal alkaline SMase.
Figure 4:
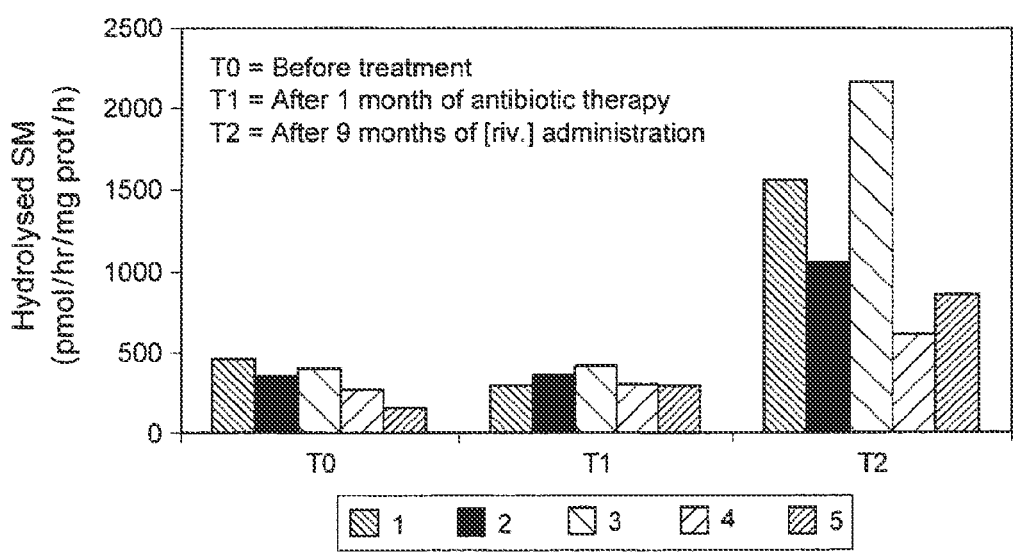
FIG. 4 shows the effect of a combination of lactic acid bacteria and bifidebacteria on intestinal alkaline SMase activity in pouchitis patients.

As shown in FIG. 3, the assay of the activity of SMase in the samples of Streptococcus thermophilus, under the experimental conditions used for the determination of intestinal SMase, showed that the bacterial enzyme was not affected by the presence or absence of bile salts. Furthermore, when the bacterial SMase activity and the intestinal SMase activity were tested simultaneously, the hydrolysis of SM increased additively. Similar results (not shown) were obtained with alkaline sphingomyelinase from the Lactobacillus brevis CD2 strain, filed on Feb. 6, 1998 under access No. DSM 11,988 in the German Collection of Microorganisms and Cell Cultures in Braunschweig, Germany ("Deutsche Sammlung von Mikroorganismen and Zellkulturen GmbH") under the Budapest Treaty, or mutants or derivatives thereof Treatment and Preventing Relapse of Pouchitis FIG. 4 shows the effect of a combination of lactic acid bacteria and bifidobacteria on intestinal alkaline SMase activity in pouchitis patients. Pouchitis is a nonspecific inflammation of the ileal reservoir and is the most common long-term complication after pouch surgery for ulcerative colitis. It is characterized by increased stool frequency, low-grade fever and extraintestinal manifestations may also occur. Pouchitis is presented here as an illustration of an inflammatory intestinal disorder and equates to an inflammatory and apoptosic processes of the intestine or an inflammatory intestinal disease.

Patients selected for the study were administered a mixture of the strains Lactobacillus casei, Lactobacillus plantarum, Lactobacillus acidophilus, Lactobacillus delbrueckii, Bifidobacterium longum, Bifidobacterium breve, and Bifidobacterium infantis. These strains are alkaline sphingomyelinase producers. Patients were selected, examined and administered the above mixture and assessed for pouchitis relapse following the procedures described in Gionchetti et al, Gasterenterology 2000; 119:305-390 (the disclosure of which is hereby incorporated by reference). FIG. 4 is a histogram of the measured alkaline SMase activity in 5 pouchitis patients assessed by mucosal biopsy using the assay described in the above Methods section. Results are reported before treatment (T0), after 1 month of antibiotic (polymyxin and kanamycin) therapy (T1) and after nine months treatment with the above mixture of probiotic bacterial strains (T2). This together with other aspects of the study demonstrate the use of a mixture of strains of alkaline sphingomyelinase-producing probiotic bacteria significantly enhance the production of alkaline sphingomyelinase and are thereby useful in the treatment of chronic relapsing pouchitis.

Increase in Intestinal Alkaline Sphingomyelinase Levels Via Food Supplement

Figure 5:
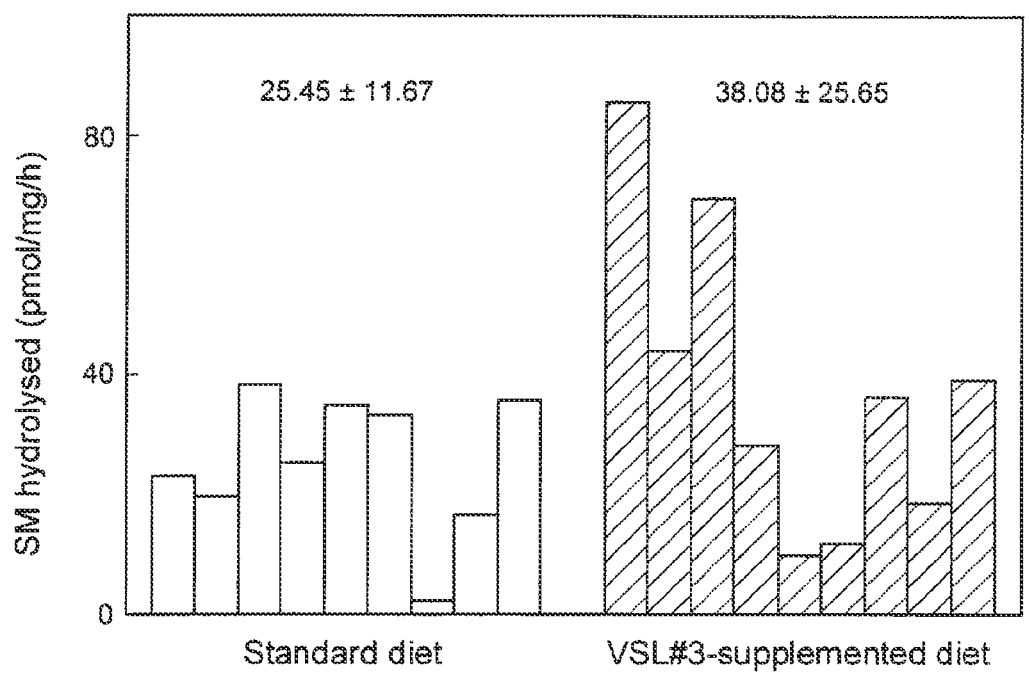
FIG. 5 shows the effect on alkaline SMase in animal (rat) tissue.

FIG. 5 shows the effect of on intestinal alkaline sphingomyelinase levels in rats with a diet supplemented with a mixture of the strains *Lactobacillus casei, Lactobacillus plantarum, Lactobacillus acidophilus, Lactobacillus delbrueckii, Bifidobacterium longum, Bifidobacterium breve,* and *Bifidobacterium infantis.*

A number of embodiments of the invention have been described. Nevertheless, it will be understood that various modifications may be made without departing from the spirit and scope of the invention. Accordingly, other embodiments are within the scope of the following claims.

What is claimed is:

1. A method of preventing or treating a disorder or disease selected from the group consisting of:
    an inflammatory process of the intestine and its associated structures;
    an apoptosic process of the intestine and its associated structures; and
    an inflammatory intestinal disorder or disease;
    said method comprising:
    (a) providing a dietetic, a nutrient or a pharmaceutical composition formulated for oral, enteral or parenteral administration comprising:
        (i) a live alkaline sphingomyelinase-expressing bacterium;
        (ii) an alkaline sphingomyelinase-expressing bacterium;
        (iii) a preparation comprising a bacterial extract comprising an alkaline sphingomyelinase-expressing bacterium;
        (iv) a preparation of lyophilized alkaline sphingomyelinase-expressing bacteria,
        wherein the live alkaline sphingomyelinase-expressing bacterium, the bacterial extract preparation or the lyophilized bacterial preparation is formulated at between about $1\times10^2$ and about $200\times10^9$ bacteria per gram of dietetic, nutrient or pharmaceutical composition; or
        (v) a combination thereof,
    and the alkaline sphingomyelinase hydrolyzes a sphingomyelin to a ceramide and a phosphorylcholine, and the hydrolysis is optimal at about pH 9,
    (b) administering a therapeutically effective amount of the dietetic, nutrient or pharmaceutical composition to a subject in need thereof,
    thereby preventing or treating the inflammatory intestinal disease or disorder, the inflammatory process of the intestine and its associated structures; or the apoptosic process of the intestine and its associated structures.

2. The method of claim 1, wherein the live alkaline sphingomyelinase-expressing bacterium, the bacterial extract preparation or the lyophilized bacterial preparation is formulated at between about $1\times10^2$ and about $150\times10^9$ bacteria per gram of dietetic, nutrient or pharmaceutical composition.

3. The method of claim 2, wherein the live alkaline sphingomyelinase-expressing bacterium, the bacterial extract preparation or the lyophilized bacterial preparation is formulated at between about $1\times10^2$ and about $4\times10^9$ bacteria per gram of dietetic, nutrient or pharmaceutical composition.

4. The method of claim 1, wherein the dietetic, nutrient or pharmaceutical composition further comprises or is formulated as an artificial milk, a condensed milk, a soybean milk, a powdered milk, a partially humanized milk or a baby food.

5. The method of claim 1, wherein the live alkaline sphingomyelinase-expressing bacterium is a lactic acid bacterium; the bacterial extract is derived from a lactic acid bacterium; or, the preparation of lyophilized alkaline sphingomyelinase-expressing bacteria is made from a lactic acid bacterium.

6. The method of claim 5, wherein the lactic acid bacterium is a *Lactobacillus brevis* CD2 strain, deposited on Feb. 6, 1998 under access No. DSM 11,988 in the German Collection of Microorganisms and Cell Cultures (DSM) in Braunschweig, Germany.

7. The method of claim 1, wherein the live alkaline sphingomyelinase-expressing bacterium, the bacterial extract preparation or the lyophilized bacterial preparation is formulated to have between about $200\times10^9$ *Streptococcus thermophilus*, $150\times10^9$ *Bifidobacteria* and $4\times10^9$ *Lactobacillus acidophilus* per gram of dietetic, nutrient or pharmaceutical composition.

8. The method of claim 1, wherein the dietetic, nutrient or pharmaceutical composition further comprises a composition selected from the group consisting of: a bile acid, an ursodeoxycholic acid, a pectin, a sphingomyelin, an arginine deiminase, a fatty acid, a polyunsaturated fatty acid, a non-fermented sugar, a lactulose, cholesterol inhibitor, a ceramidase inhibitor, a protease inhibitor, an immunomodulator, an anti-carcinogenic agent, a vitamin, a growth factor, a surfactant, a cereal, a fiber, an emulsifier, a stabilizer, a lipid, an antioxidant, a preservative, a free-radical neutralizer, a vasoprotector, and mixtures thereof.

9. The method of claim 1, wherein the dietetic, nutrient or pharmaceutical composition is formulated for enteral alimentation administration, or is in a form suitable for enteral alimentation administration.

10. The method of claim 1, wherein the dietetic, nutrient or pharmaceutical composition is formulated for pediatric administration, or is in a form suitable for pediatric administration.

11. The method of claim 1, wherein the dietetic, nutrient or pharmaceutical composition is formulated as a food supplement, or is the form of a food supplement.

12. The method of claim 1, wherein the live alkaline sphingomyelinase-expressing bacterium, the bacterial extract preparation or the lyophilized bacterial preparation comprises, or is derived from, or is derived from a preparation of: a bacterium selected from the group consisting of: *Lactobacillus acidophilus, Lactobacillus brevis, Lactobacillus buchneri, Lactobacillus casei, Lactobacillus catenaforme, Lactobacillus cellobiosus, Lactobacillus crispatus, Lactobacillus curvatus, Lactobacillus delbrueckii, Lactobacillus fermentum, Lactobacillus jensenii, Lactobacillus leichmannii, Lactobacillus minutus, Lactobacillus plantarum, Lactobacillus rogosee, Lactobacillus salivarius, Bifidobacterium adolescentis, Bifidobacterium angulatum, Bifidobacterium bifidum, Bifidobacterium breve, Bifidobacterium catenulatum, Bifidobacterium dentium, Bifidobacterium eriksonii, Bifidobacterium infantis, Bifidobacterium longum, Bifidobacterium plantarum, Bifidobacterium pseudocatenulatum, Bifidobacterium pseudolongum, Streptococcus lactis, Streptococcus raffinolactis, Streptococcus thermophilus*, and a combination thereof.

13. The method of claim 1, wherein the live alkaline sphingomyelinase-expressing bacterium, the bacterial extract preparation or the lyophilized bacterial preparation comprises, or is derived from, or is derived from a preparation of: a bacterium selected from the group consisting of:

a *Lactobacillus casei*, a *Lactobacillus plantarum*, a *Lactobacillus acidophilus*, a *Lactobacillus delbrueckii*, a *Bifidobacterium longum*, a *Bifidobacterium breve*, and a *Bifidobacterium infantis*.

14. The method of claim 13, wherein the live alkaline sphingomyelinase-expressing bacterium, the bacterial extract preparation or the lyophilized bacterial preparation comprises, or is derived from, or is derived from a preparation of at least one of each of: a *Lactobacillus casei*, a *Lactobacillus plantarum*, a *Lactobacillus acidophilus*, a *Lactobacillus delbrueckii*, a *Bifidobacterium longum*, a *Bifidobacterium breve*, and a *Bifidobacterium infantis*.

15. A method of preventing or treating a pouchitis, said method comprising:
(a) providing a dietetic, a nutrient or a pharmaceutical composition formulated for oral, enteral or parenteral administration comprising:
  (i) a live alkaline sphingomyelinase-expressing bacterium;
  (ii) a preparation comprising a bacterial extract comprising an alkaline sphingomyelinase-expressing bacterium;
  (iii) a preparation of lyophilized alkaline sphingomyelinase-expressing bacteria,
  wherein the live alkaline sphingomyelinase-expressing bacterium, the bacterial extract preparation or the lyophilized bacterial preparation is formulated at between about $1 \times 10^2$ and about $200 \times 10^9$ bacteria per gram of dietetic, nutrient or pharmaceutical composition; or
  (iv) a combination thereof,
and the alkaline sphingomyelinase hydrolyzes a sphingomyelin to a ceramide and a phosphorylcholine, and the hydrolysis is optimal at about pH 9,
wherein the live alkaline sphingomyelinase-expressing bacterium, the bacterial extract preparation or the lyophilized bacterial preparation comprises, or is derived from, or is derived from a preparation of at least one of each of: a *Lactobacillus casei*, a *Lactobacillus plantarum*, a *Lactobacillus acidophilus*, a *Lactobacillus delbrueckii*, a *Bifidobacterium longum*, a *Bifidobacterium breve*, and a *Bifidobacterium infantis*,
(b) administering a therapeutically effective amount of the dietetic, nutrient or pharmaceutical composition to a subject in need thereof,
thereby preventing or treating the pouchitis.

16. The method of claim 1, wherein the subject has a lower level of intestinal alkaline sphingomyelinase as compared to a level of intestinal alkaline sphingomyelinase in a comparable normal subject.

17. The method of claim 1, wherein the inflammatory intestinal disease or disorder, the inflammatory process of the intestine and its associated structures; or the apoptosic process of the intestine and its associated structures, comprise a pouchitis.

18. The method of claim 1, wherein the dietetic, nutrient or pharmaceutical composition formulated for oral, enteral or parenteral administration comprises a live alkaline sphingomyelinase-expressing bacterium.

19. The method of claim 1, wherein the dietetic, nutrient or pharmaceutical composition formulated for oral, enteral or parenteral administration comprises a preparation comprising a bacterial extract comprising an alkaline sphingomyelinase-expressing bacterium.

20. The method of claim 1, wherein the dietetic, nutrient or pharmaceutical composition formulated for oral, enteral or parenteral administration comprises a preparation of lyophilized alkaline sphingomyelinase-expressing bacteria,
wherein the live alkaline sphingomyelinase-expressing bacterium, the bacterial extract preparation or the lyophilized bacterial preparation is formulated at between about $1 \times 10^2$ and about $200 \times 10^9$ bacteria per gram of dietetic, nutrient or pharmaceutical composition.

* * * * *